United States Patent
Shropshire

(10) Patent No.: US 11,439,744 B1
(45) Date of Patent: Sep. 13, 2022

(54) MEDICAL EQUIPMENT MOUNTING SYSTEM FOR AN I.V. POLE

(71) Applicant: Camille Shropshire, Daytona Beach, FL (US)

(72) Inventor: Camille Shropshire, Daytona Beach, FL (US)

(*) Notice: Subject to any disclaimer, the term of this patent is extended or adjusted under 35 U.S.C. 154(b) by 0 days.

(21) Appl. No.: 17/233,690

(22) Filed: Apr. 19, 2021

(51) Int. Cl.
*A61M 5/14* (2006.01)
*A61G 7/05* (2006.01)

(52) U.S. Cl.
CPC ......... *A61M 5/1415* (2013.01); *A61G 7/0503* (2013.01); *A61M 2209/082* (2013.01)

(58) Field of Classification Search
CPC .......... A61M 5/1415; A61M 2209/082; A61G 7/0503
See application file for complete search history.

(56) References Cited

U.S. PATENT DOCUMENTS

| | | | |
|---|---|---|---|
| 4,489,454 A * | 12/1984 | Thompson | A61G 7/0503 5/503.1 |
| 4,511,158 A | 4/1985 | Varga | |
| 4,600,209 A | 8/1986 | Kerr, Jr. | |
| 4,700,922 A | 10/1987 | Gross | |
| 4,886,237 A * | 12/1989 | Dennis | A61G 7/05 248/316.5 |
| 5,149,036 A | 9/1992 | Sheehan | |
| 5,704,577 A * | 1/1998 | Gordon | F16B 7/0493 248/230.1 |
| 6,039,293 A * | 3/2000 | Minet | A61G 7/053 5/81.1 R |
| 6,179,260 B1 | 1/2001 | Ohanian | |
| 6,464,188 B1 * | 10/2002 | Donovan | A61M 5/1415 248/314 |
| 7,150,058 B2 * | 12/2006 | Rabska | A61G 7/053 5/503.1 |
| 7,258,310 B2 * | 8/2007 | Norris | A61G 5/10 248/125.7 |
| 8,336,839 B2 * | 12/2012 | Boccoleri | A61M 5/1415 248/280.11 |

* cited by examiner

*Primary Examiner* — Anita M King
(74) *Attorney, Agent, or Firm* — Sanchelima & Associates, P.A.; Christian Sanchelima; Jesus Sanchelima

(57) ABSTRACT

A medical equipment mounting system for an I.V. pole including an arm having an adjustable clamp on the distal end, and a mounting plate. The mounting plate is welded to the side of a hospital bed. Furthermore, the proximal end of the arm is attached to the mounting plate. In one embodiment, the clamp is a U-shaped clamp having a security screw disposed along its opening. The security screw allows for the I.V. pole to be safely secured to the clamp and prevents the detachment of pole when a hospital patient bed is being transported or maneuvered.

10 Claims, 3 Drawing Sheets

MEDICAL EQUIPMENT MOUNTING SYSTEM FOR AN I.V. POLE

BACKGROUND OF THE INVENTION

1. Field of the Invention

The present invention relates to medical equipment mounting system and, more particularly, to a medical equipment mounting system for an I.V. pole that includes an arm having an adjustable clamp on a distal end which receives an I.V. to ease the simultaneous transportation of the I.V. pole and a hospital patient bed.

2. Description of the Related Art

Several designs for a medical mounting system have been designed in the past. None of them, however, include a medical equipment mounting system for an I.V. pole including an arm having an adjustable clamp on the distal end, and a mounting plate. The mounting plate is welded to the side of a hospital bed. Furthermore, the proximal end of the arm is attached to the mounting plate. In one embodiment, the clamp is a U-shaped clamp having a security screw disposed along its opening. The security screw allows for the I.V. pole to be safely secured to the clamp and prevents the detachment of pole when a hospital patient bed is being transported or maneuvered. It is known that in the medical field there is often a need to transport a hospital patient bed and an I.V. pole simultaneously in order to aid a patient. Therefore, there is a need for a medical mounting system for safely transporting hospital patient beds and I.V. poles simultaneously.

Applicant believes that a related reference corresponds to U.S. Pat. No. 4,700,922 issued for a medical equipment mounting apparatus for a hospital bed. Applicant believes that another related reference corresponds to U.S. Pat. No. 4,600,209 issued for a device which is attached to a patient transport bed in a hospital wherein an intravenous bag support pole can be secured to the frame of the bed. However, the cited references differ from the present invention because they fail to disclose a mounting system including an arm having and adjustable U-shaped clamp on a distal end.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a medical mounting system for an I.V. pole which allows for the simultaneous transportation of a hospital patient bed and an I.V. pole.

It is another object of this invention to provide a medical mounting system for a hospital bed which includes minimal structure to prevent clutter associated with medical equipment.

It is still another object of the present invention to provide a medical mounting system for a hospital bed which may be either welded to the side of a bed frame or detachable to a bed frame to provide ease of use for medical staff operating the I.V. pole.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
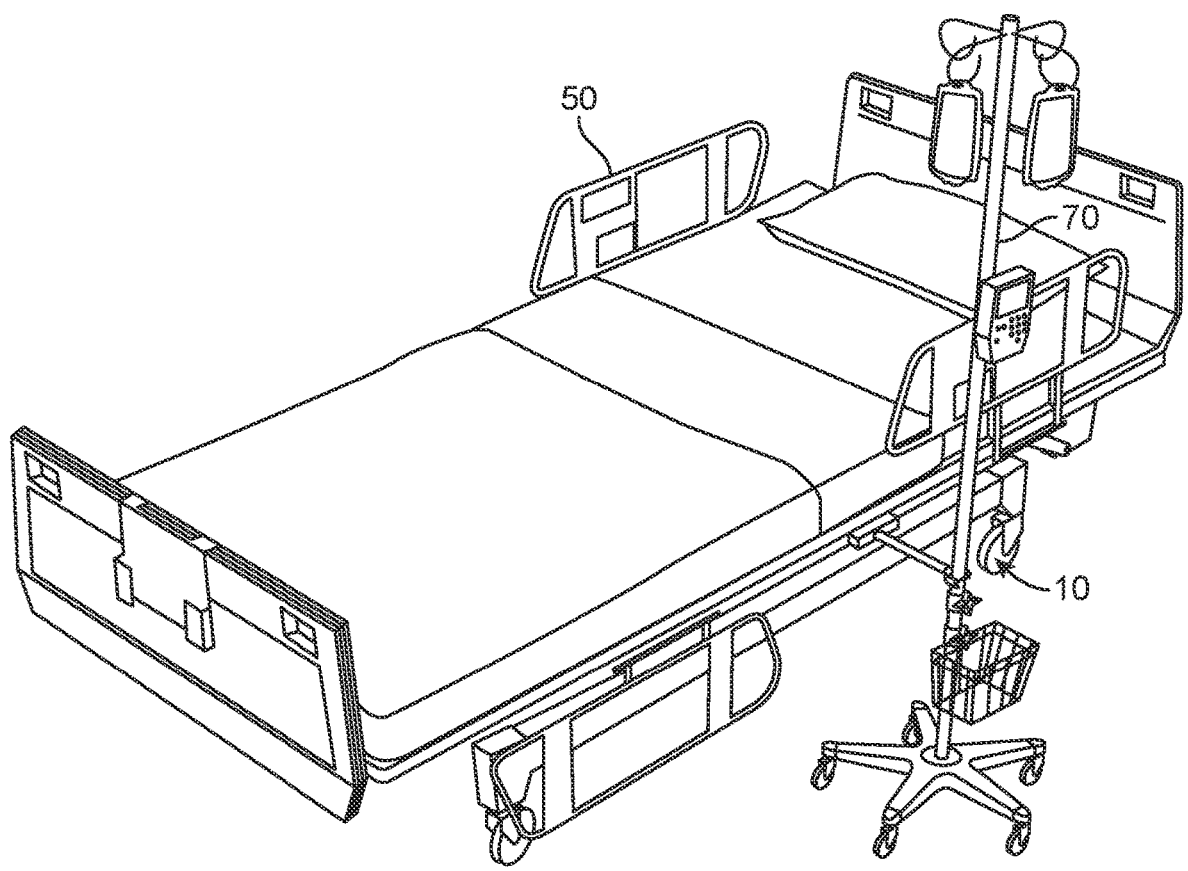
FIG. 1 represents an operational isometric view depicting the medical mounting system 10 attached to a hospital patient bed and being clamped to an I.V. pole in accordance with an embodiment of the present invention.

Referring now to the drawings, where the present invention is generally referred to with numeral 10, it can be observed a medical mounting system 10 which basically includes an arm assembly 20 and a clamp assembly 40.

Arm assembly 20 includes an arm plate 22 which is adapted to be attached to a patient bed frame 50. In on embodiment, patient bed frame 50 is a frame portion of a hospital patient bed in a hospital environment. It should be understood that any variation of a hospital patient bed may be used for the present invention. In the present implementation, arm plate 22 is a substantially cuboid structure with a rectangular shape. The arm plate may include four perimeter sidewalls and a top and bottom face. In the embodiment depicted in FIG. 2, arm plate 22 is welded directly onto the patient bed frame 50. As observed in the figure, arm plate 22 may be welded directly onto a top edge of the bade frame 50. Other embodiments may feature the arm plate 22 being secured to different locations on the patient bed frame 50. This may include having the arm plate 22 welded onto the bottom edge of the frame or along the side perimeter of the frame.

Figure 3:
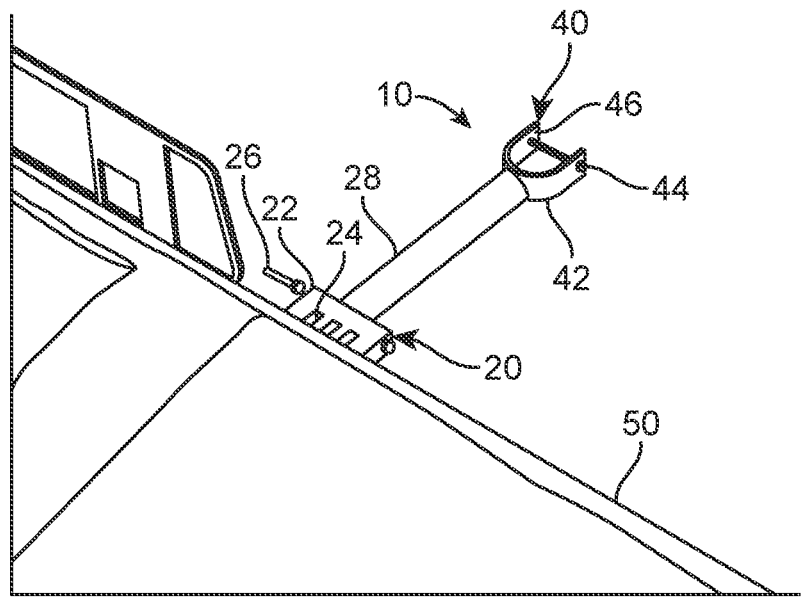
FIG. 3 illustrates an isometric view of medical mounting system 10 including an arm assembly 20 and a clamp assembly 40, the arm assembly 20 being detachable from the side of the bedframe in accordance with an embodiment of the present invention.
Figure 4:
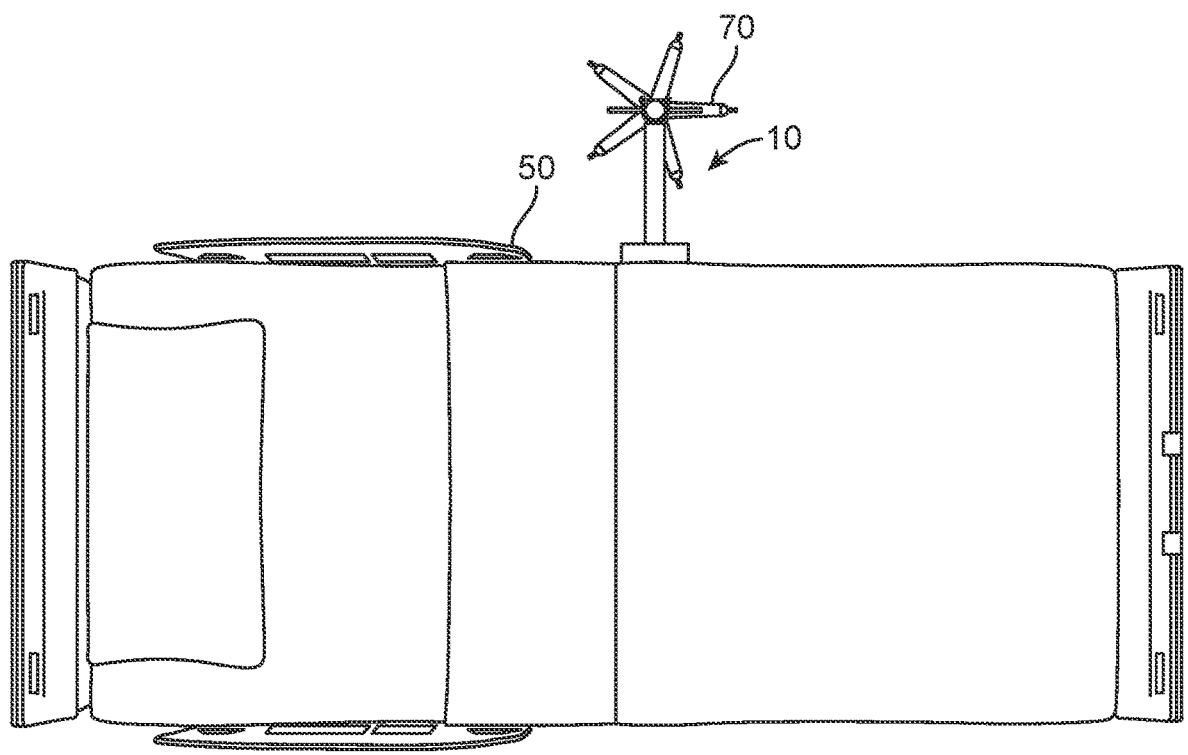
FIG. 4 is a representation of another operational isometric view depicting an I.V. pole being securely mounted to medical mounting system 10 in accordance with an embodiment of the present invention.

In the embodiment depicted in FIG. 3, arm assembly 20 further includes plate tabs 24. Plate tabs 24 may be featured as flat metallic rectangular structures being made of the same material as that of arm plate 22. Furthermore, plate tabs 24 are initially welded directly to the top edge of bed frame 50 as observed in the figure. In one embodiment, plate tabs 24 are substantially spaced apart along the top edge of bed frame 50. After being welded on the bed frame 50, arm plate 22 is then introduced onto the bed frame 50 via the pate tabs 24. Arm plate 22 is positioned directly underneath the plate tabs 24 such that plate tabs 24 are directly abutting with the top face of the arm plate 22. Plate tabs 24 are then welded onto the top face of the arm plate 22. As a result, arm plate 22 is securely mounted to the bed frame 50.

Figure 2:
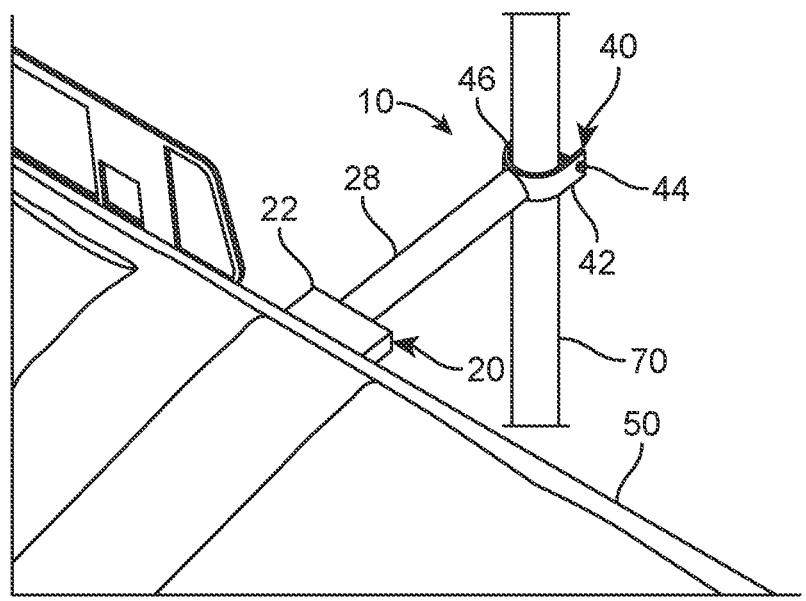
FIG. 2 shows an isometric view of medical mounting system 10 including an arm assembly 20 and a clamp assembly 40 in accordance with a welded embodiment of the present invention.

Arm assembly 20 further includes threaded bolts 26 and an arm 28. In one embodiment, arm 28 engages with arm plate 22 and extends therefrom. FIGS. 2 and 3 depict an embodiment wherein arm 28 extends perpendicularly from one of the four sidewalls of arm plate 22. Other embodiments may feature arm 28 extending from different locations of the arm plate 22. Arm 28 may be directly welded onto arm plate 22. Arm 28 also includes a distal end and a proximal end, the proximal end is the end that engages with the arm plate 22. In another implementation, arm 28 may be removably engaged to arm plate 22. To enable this removable configuration threaded bolts 26 are mounted onto the arm plate 22. As observed in FIGS. 2 and 3, threaded bolts 26 are located along opposing sidewalls of arm plate 22. In one embodiment, threaded bolts 26 may be provided as a threaded or smooth member which is inserted within arm plate 22 and engages with arm 28 effectively coupling arm 28 to arm plate 22.

Clamp assembly 40 includes a clamp 42 and a security screw 44 as observed in FIGS. 2 and 3 of the provided drawings. In one embodiment, clamp 42 is secured to the distal end of arm 28 of arm assembly 20. Additionally, clamp 42 may have a substantially U-shaped or C-shaped configuration which allows it to be used as a slot. In the present implementation, the open slot portion formed from clamp 42 receives an I.V. Pole to be secured therein. This configuration could be observed in FIGS. 1 and 2 of the provided drawings. In one embodiment, security screw 44 is provided in order to effectively lock in and mount I.V. pole 70 to clamp 42. As observed in FIG. 3, security screw 44 is a threaded screw member that extends along the open slot portion of clamp 42. A user may provide a rotational motion in order to screw in security screw 44 to extend it across the open slot portion of clamp 42 to lock I.V. pole in place. FIG. 2 depicts an embodiment wherein the I.V. pole is locked into place within clamp 42. In one embodiment, clamp 42 is also made of a metallic material similar to the material used for arm assembly 20. Furthermore, the interior curve of clamp 42 is lined with a rubber liner 46. Rubber liner 46 may be a synthetic rubber material that extends entirely along the inner side of clamp 42. Additionally, Rubber liner 46 may be formulated to have a substantially high coefficient of friction so as to further secure I.V. pole 70 when mounted therein.

In one implementation, medical mounting system 10 is implemented into a hospital patient bed in a hospital. When a patient is in need of intravenous fluids, the I.V. pole 70 is secured to a bed frame 50 of the patient via clamp assembly 40. This structure allows for the bed and I.V. pole to be transported simultaneously and eases discomfort for the medical staff and the patient.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A medical mounting system, comprising:
   a. an arm assembly including an arm plate configured to be mounted to a bed frame of a hospital patient bed, wherein said arm plate is rectangular in shape and made of a metallic material, said arm plate being mounted along an edge of said bed frame for said hospital patient bed, wherein said arm assembly further includes an arm extending outwardly from said arm plate, said arm having an proximal end abutting with said arm plate and a distal end, said arm assembly further includes threaded bolts along sidewalls of the arm plate which removably engage with said arm; and
   b. a clamp assembly including a clamp disposed on the distal end of said arm, said clamp having an open slot portion which receives an article therein, said clamp further including a security screw which extends entirely across the open slot portion to secure the article within the clamp, wherein said security screw is a threaded screw member.

2. The medical mounting system of claim 1 wherein said arm plate is abuttingly engaged to said bed frame and welded thereon of said hospital patient bed.

3. The medical mounting system of claim 1 wherein said arm assembly further includes plate tabs extending from said bed frame and abuttingly engaged to said arm plate from said hospital patient bed.

4. The medical mounting system of claim 3 wherein said plate tabs abuttingly engage a top surface of said arm plate.

5. The medical mounting system of claim 1 wherein said proximal end of said arm is perpendicularly abutting with the arm plate.

6. The medical mounting system of claim 1 wherein said article is an intravenous pole.

7. The medical mounting system of claim 1 wherein said clamp has a U-shaped configuration.

8. The medical mounting system of claim 1 wherein an inner side portion of said clamp includes a rubber liner.

9. A medical mounting system, comprising:
   a. a hospital patient bed including a bed frame;
   b. an arm assembly including an arm plate configured to be mounted to said hospital patient bed, wherein said arm plate is rectangular in shape and made of a metallic material, said arm plate including four lateral sidewalls and top and bottom faces, wherein one of said four lateral sidewalls of said arm plate is welded along an upper edge of the bed frame for said a hospital patient bed, wherein said bed frame further includes plate tabs extending from a top edge which are in abutting engagement with the top face of the arm plate, wherein said plate tabs are welded directly onto the top face, wherein said arm assembly further includes an arm extending outwardly from said arm plate in a perpendicular configuration, said arm having an proximal end abutting with said arm plate and a distal end, wherein said arm plate further includes threaded bolts along opposing lateral sidewalls thereof which secure said arm to said arm plate; and
   c. a clamp assembly including a clamp disposed on the distal end of said arm, said clamp having an open slot portion which receives an article therein, said clamp further including a security screw which extends entirely across the open slot portion to secure an article within the clamp, wherein said security screw is a threaded screw member, wherein said clamp has a U-shape configuration and includes an inner side portion and an outer side portion, wherein the inner side portion of the clamp includes a rubber liner.

10. A medical mounting system, consisting of:
   a. a hospital patient bed having a bed frame;
   b. an I.V. pole;
   c. an arm assembly including an arm plate configured to be mounted to said hospital patient bed, wherein said arm plate is rectangular in shape and made of a metallic material, said arm plate including four lateral sidewalls and top and bottom faces, wherein one of said four lateral sidewalls of said arm plate is welded along an upper edge of the bed frame for a hospital patient bed, wherein said bed frame further includes three plate tabs extending from a top edge which are in abutting engagement with the top face of the arm plate, wherein said three plate tabs are welded directly onto the top face, wherein said arm assembly further includes an arm extending outwardly from said arm plate in a perpendicular configuration, said arm having an proximal end abutting with said arm plate and a distal end, wherein said arm plate further includes threaded bolts along opposing lateral sidewalls thereof which secure said arm to said arm plate; and d. a clamp assembly including a clamp disposed on the distal end of said arm, said clamp having an open slot portion which receives said I.V. pole therein, said clamp further including a security screw which extends entirely across the open slot portion to secure an article within the clamp, wherein said security screw is a threaded screw member, wherein said clamp has a U-shape configuration and includes an inner side portion and an outer side portion, wherein the inner side portion of the clamp includes a rubber liner.

* * * * *